United States Patent [19]

Mobashery

[11] Patent Number: 5,112,751
[45] Date of Patent: May 12, 1992

[54] METHOD FOR INACTIVATING DEHYDROPEPIDASE ACTIVITY IRREVERSIBLY WITH ALKENOIC ACID COMPOUNDS

[75] Inventor: Shahriar Mobashery, Flint, Mich.

[73] Assignee: Board of Governors of Wayne State University, Detroit, Mich.

[21] Appl. No.: 651,465

[22] Filed: Feb. 6, 1991

[51] Int. Cl.$^5$ .................... C12N 9/99; C12N 9/48
[52] U.S. Cl. ........................ 435/184; 435/212
[58] Field of Search ........................ 435/184, 212

[56] References Cited

PUBLICATIONS

J. Antibiot. 32, 1 (1979).
J. Am. Chem. Soc. 100, 6491 (1979).
J. Med. Chem. 22, 1435 (1979).
Antimicrob. Agents Chemother. 22, 62 (1982).
Graham et al., J. Med. Chem. 30, 1074 (1987).
J. Natl. Cancer Inst. 7, 51 (1946).
Advances in Enzymology and Related Subjects of Biochemistry 8, 117 (1948).
J. Biol. Chem. 259, 14586 (1984).
Silverman, R. Mechanism-Based Enzyme Inactivation: Chemistry and Enzymology, CRC Press, Boca Raton (1988).
Eliel, E. L., Hartmann, A. A., J. Org. Chem. 37, 505 (1972).
J. Org. Chem. 17, 116 (1952).
Proc. Natl. Acad. Sci. U.S.A. 87, 578 (1990).
Biochem. J. 257, 361 (1989).
Methods Enzymol. 19, 722 (1970).

*Primary Examiner*—David M. Naff
*Assistant Examiner*—Mike Meller
*Attorney, Agent, or Firm*—Ian C. McLeod

[57] ABSTRACT

Alkenoic acid compounds are described. The compounds which are dehydropeptidase inactivators contain a

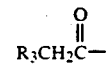

moiety which is substituted with a halomethylene or a cyano moiety as $R_3$. The enzyme deprotonates the alpha-$CH_2$ group and then the intermediate compound forms a covalent bond with enzymic residue in the active site, resulting in irreversible inactivation of the enzyme. The compounds are particularly inactivators of renal dipeptidases.

10 Claims, No Drawings

METHOD FOR INACTIVATING DEHYDROPEPIDASE ACTIVITY IRREVERSIBLY WITH ALKENOIC ACID COMPOUNDS

BACKGROUND OF THE INVENTION (1) Field of the Invention

The present invention relates to alkenoic acid compounds which are inactivators of dehydropeptidases. In particular, the present invention relates to alkenoic acid compounds which contain a 2-halo ethylene or cyanomethylene substituted carbonyl functions which serve as mechanism-based inactivators for the said enzymes.

(2) Prior Art

Thienamycin and certain thienamycin derivatives (J. Antibiot. 32, 1 (1979); J. Am. Chem. Soc. 100, 6491 (1979); J. Med. Chem. 22, 1435 (1979)), known collectively as carbapenems, are broad spectrum beta-lactam antibacterial agents. These antibiotics are stable towards the action of microbial beta-lactamases, the enzymes that traditionally catalyze the hydrolytic breakdown of beta-lactam antibiotics. However, they were shown to be hydrolyzed by mammalian renal dipeptidases (dehydropeptidase I, EC 3.4.13.11). As the product(s) of the enzymic turnover of carbapenems lack antibacterial property (Antimicrob. Agents Chemother. 22, 62 (1982)), there exists a need for specific inhibitors-/inactivators for these enzymes. The inhibitor could be used in clinical preparations in conjunction with carbapenems, with the expectation that it would inhibit renal dipeptidase, thereby allowing for prolonged availability of the antibacterial agent in vivo. One reversible inhibitor, cilastatin, has been introduced into clinical use recently and is one of a series of alkenoic acid compounds described by Graham et al (J. Med. Chem. 30, 1074 (1987)). Considerably higher levels of dehydropeptidase activity have been noted in tumors (J. Natl. Cancer Inst 7, 51 (1946)) and in cases of liver disease (Advances in Enzymology and Related Subjects of Biochemistry 8, 117 (1948)), therefore inhibitors of this enzyme could have antineoplastic properties as well. In addition, as microorganisms possess similar enzymes, these inhibitors could be antimicrobial agents. Thus, such inhibitors are of considerable interest Renal dipeptidase belongs to a class of hydrolytic enzymes referred to as metalloproteases or metallopeptidases. These enzymes sequester a catalytically important metal in their active sites. The significant metal in vivo appears to be zinc. The porcine (Methods Enzyme vol. 19, 722 (1970)) and the human renal dipeptidase (J. Biol. Chem. 259, 14586 (1984)) have been purified and shown to have similar catalytic properties. The enzyme is a dipeptidase that requires an L-amino acid at the N-terminus, however, it accommodates L-, D- or dehydro amino acids at the C-terminus. A necessity for the presence of a free amino group at the N-terminus of peptide substrates has been documented, albeit that requirement is absent for unsaturated peptides of dehydroalanine (Advances in Enzymology and Related Subjects of Biochemistry 8, 117 (1948)).

In the design of compounds with potential biological properties, specificity of targeting is of utmost importance. One class of such molecules that often afford very high specificity in inhibiting their targeted enzymes are mechanism-based inactivators ("suicide substrates"). These molecules possess structural elements that are recognized by the target enzyme, allowing for the binding of the molecule to the enzyme active site with high affinity. Subsequently, the enzyme carries out a chemical transformation that results in the formation of an electrophilic species. Since amino acid residues with nucleophilic functionalities often exist in the active sites of enzymes, the electrophilic species may modify such active site residues covalently. The enzyme, modified in the active site, is inactivated irreversibly and is incapable of catalytic turnover (Silverman, R. Mechanism-Based Enzyme Inactivation: Chemistry and Enzymology, CRC Press, Boca Raton, pp 3-12, 1988). Both molecular recognition for initial non-covalent binding of the inhibitor by the enzyme to give the enzyme-inhibitor complex (EI), and the enzyme-mediated chemical transformation of EI work in concert to afford irreversible inactivation of the targeted enzyme with high specificity.

OBJECTS

It is therefore an object of the present invention to provide novel alkenoic acid compounds which abolish the dehydropeptidase activity irreversibly and a method for the use of such compounds. In particular, it is an object of the present invention to provide alkenoic acid compounds which can be combined with carbapenem antibacterial agents to prevent the dehydropeptidase activity from hydrolyzing the carbapenem. These and other objects will become increasingly apparent from the following description.

GENERAL DESCRIPTION

The present invention relates to an alkenoic acid compound of the formula:

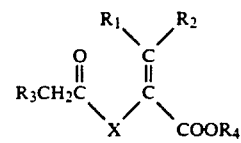

wherein $R_1$ is selected from the group consisting of hydrogen and aliphatic and aromatic moieties containing between about 1 and 12 carbon atoms and optionally atoms selected from the group consisting of sulfur, oxygen and nitrogen atoms, $R_2$ is hydrogen, $R_3$ is selected from the group consisting of cyano and halomethylene where the halide is selected from the group consisting of fluoro, chloro and bromo moieties, X is selected from the group consisting of —O—, —CH$_2$— and —NH— moieties, $R_4$ is selected from the group consisting of hydrogen, ester groups, particularly those that are readily hydrolyzable in vivo, selected from the group consisting of 3-phthalidyl, 4-crotonolactonyl, gamma-butyrolacton-4-yl, lower alkanoylmethyl and the like, and suitable salts of the carboxylate, typically inorganic salts such as sodium, potassium, lithium etc., or organic salts with typical organic amines such as lower alkyl amines, and wherein the compound inactivates a peptidase or protease irreversibly.

Further the present invention relates to a method for inactivating a peptidase or protease irreversibly which comprises: providing the peptidase or protease with an alkenoic acid compound of the formula:

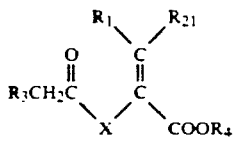
(1)

wherein X is selected from the group consisting of —O—, —CH₂— and —NH— moieties, $R_1$ is selected from hydrogen and an aliphatic and aromatic moieties containing 1 to 12 carbon atoms, $R_2$ is hydrogen, and $R_3$ is selected from the group consisting of halomethylene and cyano wherein the halide selected from chloro, fluoro and bromo moieties, and $R_4$ is selected from the group consisting of hydrogen, ester groups, particularly those that are readily hydrolyzable in vivo, selected from the group consisting of 3-phthalidyl, 4-crotonolactonyl, gamma-butyrolacton-4-yl, lower alkanoylmethyl and the like, and suitable salts of the carboxylate, typically inorganic salts such as sodium, potassium, lithium etc., or organic salts with typical organic amines such as lower alkyl amines; and reacting the enzyme with the alkenoic acid compound is inactivated irreversibly.

Finally, the present invention relates to a composition which comprises: a carbapenem antibiotic and an inactivator compound of the formula:

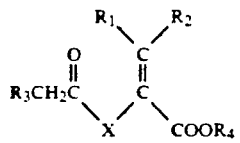

wherein $R_1$ is selected from the group consisting of hydrogen and aliphatic and aromatic moieties containing between about 1 and 12 carbon atoms and optionally atoms selected from the group consisting of sulfur, oxygen and nitrogen atoms, $R_2$ is hydrogen, $R_3$ is selected from the group consisting of cyano and halomethylene, wherein halide is selected from the group consisting of fluoro, chloro and bromo moieties and wherein X is selected from the group consisting of —O—, —CH₂— and —NH— moieties and $R_4$ is selected from the group consisting of hydrogen, ester groups, particularly those that are readily hydrolyzable in vivo, selected from the group consisting of 3-phthalidyl, 4-crotonolactonyl, gamma-butyrolacton-4-yl, lower alkanoylmethyl and the like, and suitable salts of the carboxylate, typically inorganic salts such as sodium, potassium, lithium etc., or organic salts with typical organic amines such as lower alkyl amines, wherein the inactivator compound is present in the composition in an amount which irreversibly modifies a target peptidase and prevents the peptidase from inactivating the antibiotic. Preferably the ratio of antibiotic to compound is between about 2 to 1 and 1 to 2.

In particular the present invention relates to compounds of the formula:

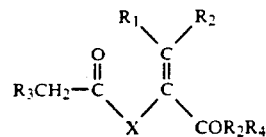

wherein $R_1$ is

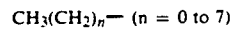
$CH_3(CH_2)_n$— (n = 0 to 7)

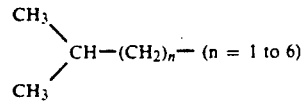
(n = 1 to 6)

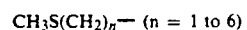
$CH_3S(CH_2)_n$— (n = 1 to 6)
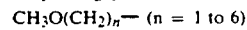
$CH_3O(CH_2)_n$— (n = 1 to 6)

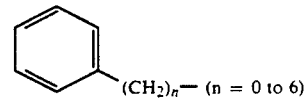
$(CH_2)_n$— (n = 0 to 6)

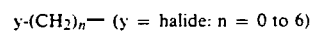
y-$(CH_2)_n$— (y = halide: n = 0 to 6)

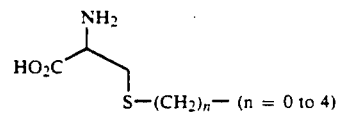
S—$(CH_2)_n$— (n = 0 to 4)

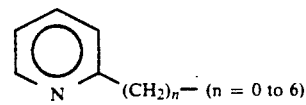
$(CH_2)_n$— (n = 0 to 6)

$R_2$ is hydrogen, $R_3$ is a cyano or a halomethylene group and X is —CH₂— or —NH— or —O—. $R_4$ is hydrogen or can be groups which provide esters as set forth above. Primarily the ester group must be hydrolyzed in vivo in order not to interfere with the activity of the compound.

The present invention particularly relates to alkenoic acid compounds which are inhibitors for renal dipeptidase. These inhibitors bind the active site of renal dipeptidase. Subsequent to this binding, the enzyme abstracts a proton from the alpha-position to the amide carbonyl in peptides or the alpha-position in ketonic molecules. The deprotonation step may be carried out by the active site zinc-bound water/hydroxide or by a side-chain functionality of an active site amino acid residue. The alkenoic acid compounds take advantage of the deprotonation (enolization) reaction to activate a "latent" functionality, resulting in the electrophilic species that modifies the protein.

This proposed mechanism is illustrated for a peptidic inactivator by the following reactions, which are believed to be operating:

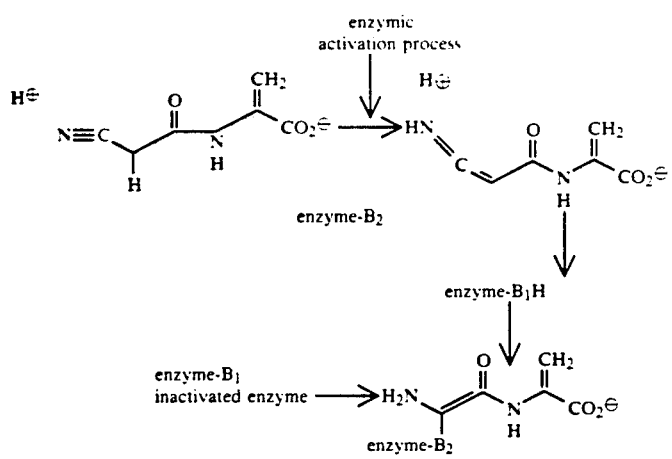

Thus, the alpha-cyanomethylene group rearranges to a ketenimine upon enzymic deprotonation and reprotonation at the nitrile nitrogen. Where $R_3$ contains a beta-halo group, the alpha-proton abstraction leads to elimination of the halide resulting in an alpha-beta-unsaturated carbonyl. The electrophilic ketenimine and the alpha-beta unsaturated carbonyl are groups that trap active site nucleophilic residues in the course of enzyme inactivation.

The reactions of enzymic turnover and inactivation are competing processes. As a result of the turnover, the inactivators are converted to product(s) that diffuse away from the active site.

With the compounds of the present invention, the "Michaelis complex" of the enzyme and inactivator (EI) proceed via the steps leading to inactivation chemistry. The ratio of the rate constants for the turnover divided by that of enzyme inactivation (i.e., $k_{cat}/k_{inact}$) is defined as the partition ratio for the inactivator. This ratio is readily measured by those skilled in enzymology and is a crucial parameter in evaluating the efficacy of each inactivator. A partition ratio of less than 5000 is desirable. Indeed, the partition ratios determined for a series of mechanism-based inactivators may prove useful in designing strategies for modulating the activity of the targeted enzyme. An inactivator exhibiting very low partition ratio may inactivate the enzyme essentially completely. On the other hand, one with a somewhat elevated partition ratio may decrease the activity of enzyme without a total shutdown of its activity. The latter kind is especially useful in inactivation of enzymes with undesirably elevated, yet crucial, physiological functions. The partition ratio, along with the reversible inhibitor constant $K_i$ (i.e., the dissociation constant for the EI complexes) are essential parameters in judging the specificity of targeting for a given enzyme in comparison with other related enzymes. Both lower $K_i$ values and lower partition ratios argue for specificity in inactivation of one enzyme versus others of the set.

SPECIFIC DESCRIPTION

Nearly all of the target amide molecules were prepared in a one-pot reaction between an alpha-keto carboxylic acid and a primary amide; this is a reaction that is applicable to a wide variety of function present on the two reagents. The primary amide can typically be cyanoacetamide, chloropropionamide, bromoacetamide (to give useful intermediates, the bromoacetyl analogues, for further synthetic elaboration) and the like. A number of keto acids of interest are commercially available. Those not available were prepared from dithiane by the methodology described by Eliel and Hartmann (Eliel, E. L., Hartmann, A. A. J. Org. Chem. 37, 505 (1972)).

The enol esters are readily made by allowing these keto acids to react with 2 equiv. of strong base, followed by reaction with an acylating agent such as N-hydroxysuccinamide ester of cyanoacetic acid or beta-halopropionic acid. The ketonic compounds are prepared readily by reaction of the lithium salt of acetonitrile with the corresponding 3-substituted-2-(carbomethoxymethyl)-propenoic acid.

EXAMPLE 1

2-Methylene-5-cyano-4-oxopentanoic acid (I).

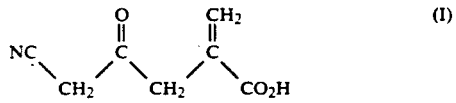

A solution of anhydrous acetonitrile (0.85 mL, 15.2 mmol) in 30 mL dry THF was stirred at −78° C. for 10 minutes under a nitrogen atmosphere. A 2.5 M solution of n-butyllithium in hexane (6.1 mL, 15.2 mmol) was added dropwise over a period of 5 minutes and the resultant solution was allowed to stir at −78° C. for 1 hour. Subsequently, a solution of 2-(carbomethoxymethyl)-propenoic acid (1.1 g, 7.6 mmol), prepared previously as described elsewhere (J. Org. Chem. 17, 116 (1952)), in 5 mL dry THF was added to the reaction mixture After stirring at −78° C. for 1 hour, the solution was gradually warmed to 0° C. and was allowed to age for 1 additional hour at this temperature. The reaction was quenched by the addition of acetic acid (~5 mL), and then was diluted with saturated $CaCl_2$. The mixture was extracted with ethyl acetate (3x), and the combined ethyl acetate fraction was washed with water, followed by drying over anhydrous $MgSO_4$. The solution was evaporated to dryness in vacuo to give an oil. The product mixture was purified on a silica gel column to afford the title compound (I) (0.81 g, 70%).

In like manner the following compounds are prepared from the appropriate reactants; i.e. the lithium salt of acetonitrile and a corresponding 3-substituted-2-(carbomethoxymethyl)-propenoic acid analogue; the Z isomers often predominate. but mixtures of E and Z are separated by chromatography on silica gel.

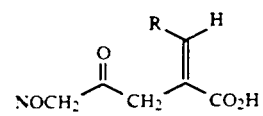

R =
—CH₃
—CH₂CH₃
—CH₂CH₂CH₃
—CH₂CH₂CH₂CH₂CH₂CH₂CH₃

—CH₂CH₂CH(CH₃)CH₃

—CH₂CH₂CH₂CH₂Br
—CH₂CH₂CH₂CH₂—S—CH₃
—CH₂CH₂CH₂CH₂—O—CH₃

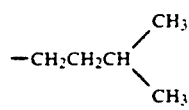

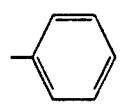

EXAMPLE 2

2-Bromoacetamidoacrlic acid (II)
(2-(bromoacetamido)-2-propenoic acid) (an intermediate).

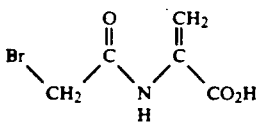

A solution of bromoacetamide (1.38 g, 10 mmol) and pyruvic acid (1.53 g, 30 mmol) in 30 mL toluene was refluxed overnight in a Dean-Stark apparatus. Subsequently, the solution was allowed to cool to room temperature, during which time a yellow solid precipitated. The solid was filtered, and then was dissolved in ether (10 mL). The solution was filtered and the insoluble material was discarded. The solvent was evaporated to dryness and the residue was recrystallized twice from benzene to afford 1.22 g of the desired product (II). Yield 59%.

In like manner the following compounds are prepared from the appropriate reactants; i.e. bromoacetamide and a corresponding 3-substituted pyruvic acid;

the Z isomers often predominate. but mixtures of E and Z are separated by chromatography on silica gel.

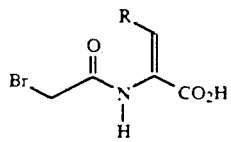

R =
—CH₃
—CH₂CH₃
—CH₂CH₂CH₂CH₂CH₂CH₂CH₃

—CH₂CH₂CH(CH₃)CH₃

—CH₂CH₂CH₂CH₂—S—CH₃
—CH₂CH₂CH₂CH₂—O—CH₃

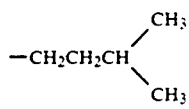

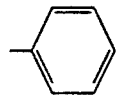

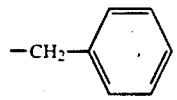

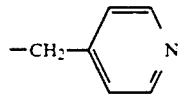

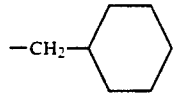

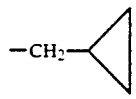

2-Cyanoacetamidoacrylic Acid (III)
(2-cyanoacetomidopropenoic acid)

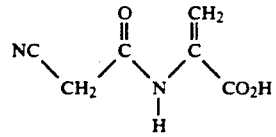

A solution of 2-bromoacetamidoacrylic acid (0.4 g, 1.9 mmol) and KCN (0.27 g, 4.1 mmol) in 25 mL methanol was stirred in the dark for 6 hours. Subsequently, acetic acid (1.5 mL) was added and the mixture was concentrated in vacuo. The concentrated solution was mixed with saturated CaCl₂ and the resultant solution was extracted with ethyl acetate (3x). The combined organic layer was washed with water, dried over MgSO₄ and evaporated in vacuo to afford the product as a white solid (III).

Similarly all alpha-bromoacetyl derivatives shown above in the first entry for Example 2 are converted to the corresponding alpha-cyano derivatives.

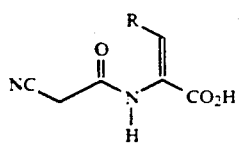

R =
—CH₃
—CH₂CH₃
—CH₂CH₂CH₂CH₂CH₂CH₂CH₃

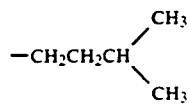

—CH₂CH₂CH₂CH₂—S—CH₃
—CH₂CH₂CH₂CH₂—O—CH₃

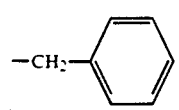

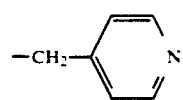

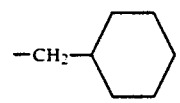

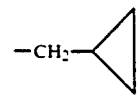

EXAMPLE 3

2-Chloropropionamide-2-propenoic acid (IV).

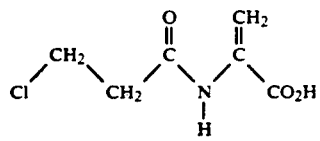

A solution f beta-chloropropionamide (8 mmol, 860 mg), pyruvic acid (11 mmol, 765 μL) and p-toluenesulfonic acid (76 mg) in 30 mL of toluene was refluxed in a Dean-Stark apparatus containing 5 Å molecular sieves overnight. The solvent was subsequently removed in vacuo to give an oil. The oil was subjected to column chromatography on silica gel to afford the title compound (IV).

EXAMPLE 4

(Z)-2-Chloropropionamide-2-butenoic acid (V).

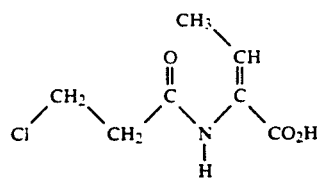

A solution of chloropropionamide (1.15 g, 10.7 mmol) and alpha-ketobutyric acid (1.1 g, 7.5 mmol) in 50 mL toluene was refluxed for 20 hours in a Dean-Stark apparatus. The solvent was removed in vacuo and the resultant oil was taken up in 50 mL ethyl acetate. The solution was stored at −20° C. overnight The excess chloropropionamide precipitated overnight, which was removed by filtration. The filtrate was concentrated to dryness to give a pale-yellow oil which was made up of an equal mixture of the E and Z isomers. The desired Z isomer (V) was purified on a silica gel column.

EXAMPLE 5

(Z)-2-Chloropropionamide-3-phenyl-2-propenoic Acid (VI)

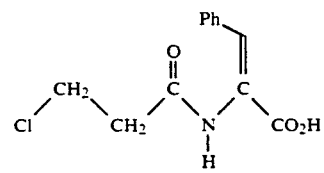

This compound (VI) is prepared as described for 2-chloropropionamide-2-propenoic acid by substituting phenylpyruvic acid for pyruvic acid.

In like manner the following compounds are prepared from the appropriate reactants; i.e. beta-chloropropionamide and a corresponding 3-substituted pyruvic acid; the Z isomers often predominate, but mixtures of E and Z are separated by chromatography on silica gel.

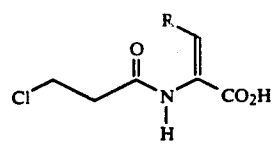

R =
—CH₃
—CH₂CH₃
—CH₂CH₂CH₂CH₂CH₂CH₂CH₃

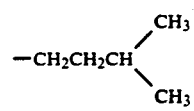

—CH₂CH₂CH₂CH₂—S—CH₃
—CH₂CH₂CH₂CH₂—O—CH₃

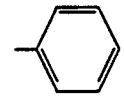

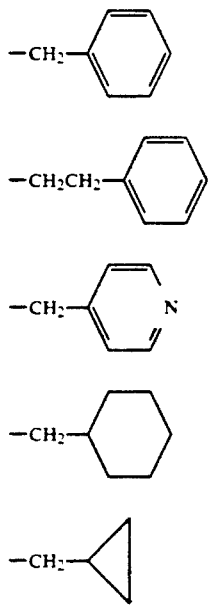

EXAMPLE 6

(Z)-7-Bromo-2-bromoacetamido-2-heptenoic Acid (an intermediate) (VII)

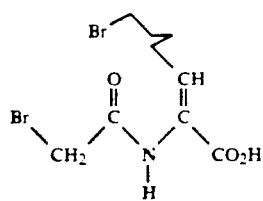

A solution of bromoacetamide (0.48 g, 3.5 mmol), 7-bromo-2-oxo-pentaoic acid (1.14 g, 5 mmol) and 35 mg p-toluenesulfonic acid was refluxed in 15 mL toluene for 4.5 hours. The solution was cooled to room temperature and was extracted with 10% $K_2CO_3$ (4x). The combined aqueous layer was washed twice with ether, and then was acidified to pH 1.0 with conc. HCl. The solution was extracted with (3x). The combined organic layer was washed with water (2x) and dried over anhydrous $MgSO_4$. The solvent was evaporated in vacuo to give an oil. The oil was crystallized from nitromethane to afford the title compound (VII).

(Z)-7-Bromo-2-cyanoacetamido-2-heptenoic acid (VIII)

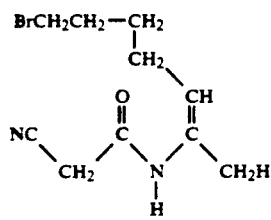

A solution of (Z)-7-bromo-2-bromoacetamido-2-heptenoic acid (70 mg, 0.201 mmol) and KCN (26.5 mg, 0.408 mmol) in 10 mL methanol was stirred for 8 hours at room temperature. A 1 mL portion of glacial acidic acid was added, followed by removal of most of the solvent in vacuo. Saturated $CaCl_2$ (~5 mL) was added and the mixture was extracted with ethyl acetate (3x). The organic layers were combined, washed with water, dried over $MgSO_4$ and evaporated to dryness. The residue was purified by column chromatography on silica gel to give the title compound (VIII).

EXAMPLE 7

(Z)-7-(2R)-(2-Amino-2-carboethoxyethyl)thiol-2-cyanoacetamido-2-heptenoic acid (IX)

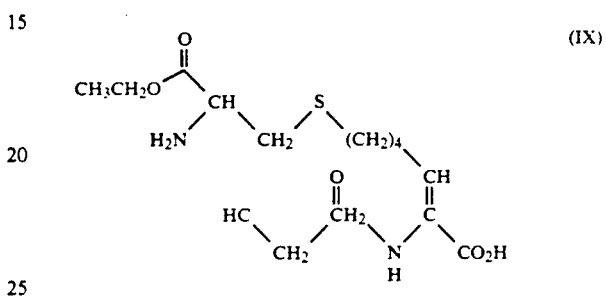

To a solution of (Z)-7-bromo-2-cyanoacetamido-2-heptenoic acid (100 mg, 0.36 mmol) in 10 mL methanol a solution of freshly prepared O-ethyl cysteine (48 mg, 0.4 mmol) in 5 mL methanol was added, followed by the addition of triethylamine (55 μL, 0.4 mmol). The solution was allowed to stir at room temperature over night. The solvent was removed in vacuo and the residue was purified over silica gel to give the desired product (IX).

EXAMPLE 8

(Z)-7-[(2R)-(2-Amino-2-carboxy)thiol-2-cyanoacetamido-2-heptenoic acid (X).

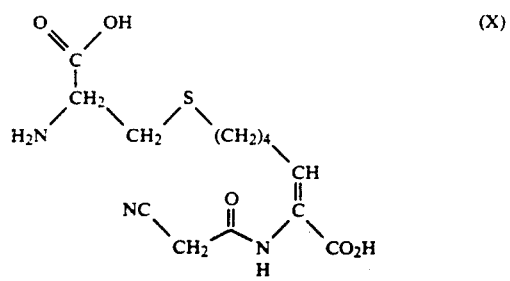

The saponifcation of the ethyl ester of compound IX can be carried out in a number of ways. The following is given as a sample of such a reaction.

A 50 mg portion of IX is suspended in 5 mL water. The pH is adjusted to 7.0 by dropwise addition of 1N NaOH at 0° C. A 20% solution of NaOH (15 mL), which is cooled previously to −20° C., is added in one portion. The resulting mixture is stirred at −10° C. for 5 minutes and then quenched by the rapid addition of glacial acidic acid (5 ml, room temperature) The mixture is applied to a column of activated carbon and the column is eluted with water. The fractions that contained the title compound (X) are combined and lyophilized.

EXAMPLE 9

2-(Cyanoacetoxy)-propenoic acid (XI).

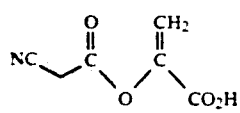 (XI)

A solution of pyruvic acid (10 mmol) in 30 mL dry THF is stirred at −78° C. for 10 minutes under a nitrogen atmosphere. A 2.5 M solution of n-butyllithium in hexane (20 mmol) is added dropwise over a period of 2 minutes and the resultant solution is aged for 1 hour at −78° C. A solution N-hydroxylsuccinimide ester of cyanoacetic (10 mmol) in 20 mL dry THF is added over 10 minutes, followed by warming of the solution to room temperature over 2 hours. A 10 mL portion of glacial acidic acid is added to the solution, and then THF is removed in vacuo. The concentrated solution is diluted with ethyl acetate and the resultant solution is washed with water (2x), followed by drying over anhydrous MgSO$_4$. The solution is evaporated to dryness, and the residue is purified on silica gel to give the title compound (XI).

In like manner the following compounds are prepared from the appropriate reactants; i.e. N-hydroxysuccinimide ester of cyanoacetic acid and a corresponding 3-substituted pyruvic acid; the Z isomers of ten predominate, but mixtures of E and Z are separated by chromatography on silica gel.

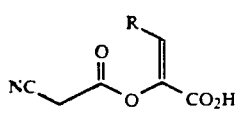

R =
—CH$_3$
—CH$_2$CH$_3$
—CH$_2$CH$_2$CH$_2$CH$_2$CH$_2$CH$_2$CH$_3$

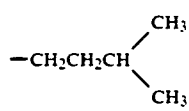

—CH$_2$CH$_2$CH$_2$CH$_2$—S—CH$_3$
—CH$_2$CH$_2$CH$_2$CH$_2$—O—CH$_3$

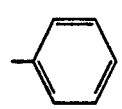

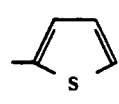

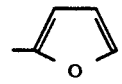

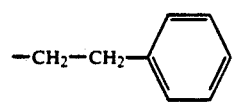

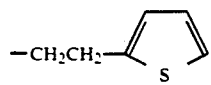

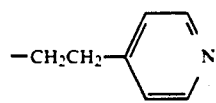

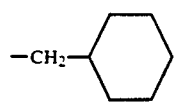

EXAMPLE 10

2-(beta-Chloropropanoyloxy)-propenoic acid (XII)

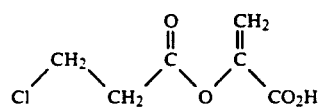 (XII)

The synthesis is as described for 2-(cyanoacetoxy)-propenoic acid, with the exception that N-hydroxysuccinimide ester of beta-chloropropenoic acid was used.

In like manner the following compounds are prepared from the appropriate reactants; i.e. N-hydroxysuccinimide ester of beta-chloropropenoic acid and a corresponding 3-substituted pyruvic acid; the Z isomers often predominate, but mixtures of E and Z are separated by chromatography on silica gel.

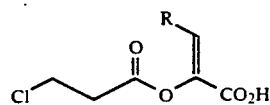

R =
—CH$_3$
—CH$_2$CH$_3$
—CH$_2$CH$_2$CH$_2$CH$_2$CH$_2$CH$_2$CH$_3$

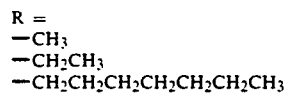

—CH$_2$CH$_2$CH$_2$CH$_2$—S—CH$_3$
—CH$_2$CH$_2$CH$_2$CH$_2$—O—CH$_3$

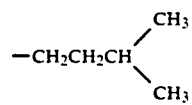

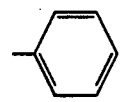

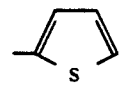

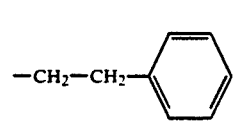

-continued

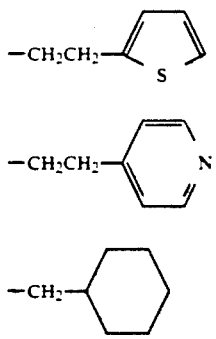

EXAMPLE 11

The kinetic analyses of the compounds of Examples 1 and 2 were carried out according to the methodology described before (Proc Natl. Acad. Sci. USA 87, 578 (1990)) and they are given here for the purpose of demonstration. $K_m$ is the Michaelis complex for the turnover, and $K_i$ is the reversible inhibitor constant for the formation of the EI complex. The parameters $k_{cat}$ and $K_{inact}$ are first-order rate constant for enzymic turnover and inactivation, respectively. The partition ratio is defined as $k_{cat}$ divided by $k_{inact}$ (i.e., $k_{cat}/k_{inact}$).

Renal dipeptidase from porcine kidney was purified by a slight modification of the literature report (Biochem. J. 257, 361 (1989)). The spectrophotometric assay of renal dipeptidase is carried out according to the method of Campbell et al. (Methods Enzymol. 19, 722 (1970)), using glycinyldehydrophenylalanine as substrate. The substrate was synthesized according to the literature report (Synthesis Commun., 234 (1982)).

The relevant kinetic parameters for interactions of I and III with porcine dehydropeptidase I are given below.

| Compound: | (III) | (I) |
|---|---|---|
| $K_m$ (mM) | 0.416 ± 0.036 | 10.30 ± 0.78 |
| $K_i$ (μM) | 18 ± 6 | 38 ± 1 |
| $k_{cat}$ (min$^{-1}$) | 15.2 ± 1.9 | 31.8 ± 8.6 |
| $k_{inact}$ (min$^{-1}$) | 0.277 ± 0.024 | 0.151 ± 0.012 |
| $k_{cat}/k_{inact}$ | 55 ± 2 | 217 ± 37 |

The above results indicate that between compounds III and I, the amide compound (I) is somewhat better than the ketonic compound (III), but that both are very effective inactivators.

It will be appreciated that the position of $R_1$ and $R_2$ in the following claixs is not necessarily indicative of the actual position. Where $R_1$, as shown, is substituted and $R_2$ is hydrogen, this is the Z isomer. Where $R_2$ is substituted and, $R_1$ is hydrogen as shown, then this is the E isomer. The Z isomers are preferred.

It is intended that the foregoing description be only illustrative of the present invention and that the present invention be limited only by the hereinafter appended claims.

I claim:

1. A method for inactivating a dehydropeptidase irreversibly which comprises:

(a) providing the dehydropeptidase with an alkenoic acid compound of the formula:

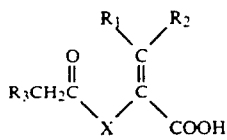

wherein X is selected from the group consisting of —O—, —CH$_2$— and —NH— moieties and R$_1$ is selected from hydrogen and aliphatic and aromatic moieties containing 1 to 12 carbon atoms, and R$_2$ is hydrogen, R$_3$ is selected from the group consisting of halomethylene and cyano; and (b) reacting the dehydropeptidase with the alkenoic acid compound to inactivate the dehydropeptidase irreversibly.

2. The method of claim 1 wherein the aliphatic and aromatic moieties also contain atoms selected from the group consisting of: sulfur, oxygen and nitrogen.

3. A method for inactivating a dehydropeptidase irreversibly which comprises:

(a) providing the dehydropeptidase with an alkenoic acid compound of the formula:

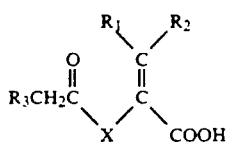

wherein X is selected from the group consisting of —O—, —CH$_2$— and —NH— moieties and R$_1$ is selected from hydrogen and lower alkyl containing 1 to 8 carbon atoms and, R$_2$ is hydrogen, R$_3$ is selected from the group consisting of halomethylene, halo being selected from the group consisting of fluoro, chloro and bromo, and cyano; and (b) react the dehydropeptidase with the alkenoic acid compound to inactivate the dehydropeptidase.

4. The method of claim 3 wherein X is the —CH$_2$— moiety.

5. The method of claim 3 wherein X is the —NH— moiety.

6. The method of claim 3 wherein R$_1$ and R$_2$ are hydrogen and X is the —CH$_2$— moiety.

7. The method of claim 3 wherein R$_1$ and R$_2$ are hydrogen and X is the —NH— moiety.

8. The method of claim 3 wherein R$_1$ and R$_2$ are hydrogen, R$_3$ is bromo and X is the —NH— moiety.

9. The method of claim 3 wherein R$_1$ and R$_2$ are hydrogen, R$_3$ is cyano and X is the —NH— moiety.

10. The method of claim 3 wherein R$_1$ and R$_2$ are hydrogen, R$_3$ is cyano and X is the —CH$_2$— moiety.

* * * * *

UNITED STATES PATENT AND TRADEMARK OFFICE
CERTIFICATE OF CORRECTION

PATENT NO. : 5,112,751
DATED : May 12, 1992
INVENTOR(S) : Shahriar Mobashery

It is certified that error appears in the above—identified patent and that said Letters Patent is hereby corrected as shown below:

Title Page, in the Title, "Dehydropepidase" should be --Dehydropeptidase--.

Column 1, in the Title, "Dehydropepidase" should be --Dehydropeptidase--.

Column 1, line 49, "Enzyme" should be --Enzymol.--.

Column 5, the first equation should be as follows:

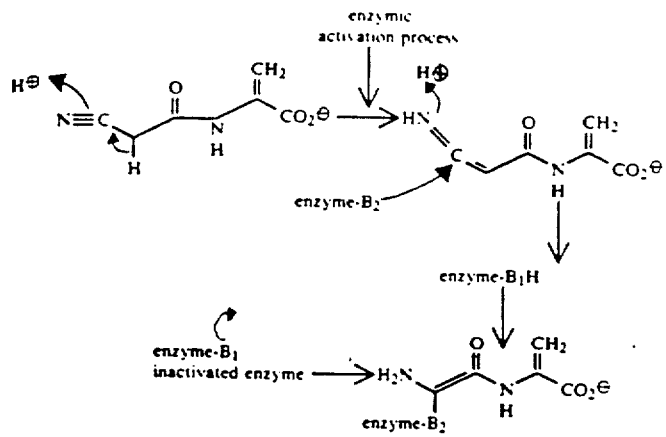

UNITED STATES PATENT AND TRADEMARK OFFICE
CERTIFICATE OF CORRECTION

PATENT NO. : 5,112,751

DATED : May 12, 1992

INVENTOR(S) : Shahriar Mobashery

It is certified that error appears in the above-identified patent and that said Letters Patent is hereby corrected as shown below:

Column 6, line 54, insert a period --.-- after "mixture" and before "After".

Column 7, first equation, "NOCH$_2$" should be --NCCH$_2$--.

Column 7, line 44, "2-Bromoacetamidoacrlic" should be --2-Bromoacetamidoacrylic--.

Column 9, line 59, "f" should be --of--.

Column 9, line 63, "5 Å" should be --4 Å--.

Column 11, line 42, "pentaoic" should be --pentanoic--.

Column 11, line 48, after "with" and before "(3x)", --ether-- should be inserted.

Column 12, first equation, "HC" should be --NC--.

Column 15, line 58, "claixs" should be --claims--.

Column 16, line 53, "react" should be --reacting--.

Signed and Sealed this

Second Day of November, 1993

Attest:

BRUCE LEHMAN

Attesting Officer     Commissioner of Patents and Trademarks